(12) United States Patent
Huemer et al.

(10) Patent No.: US 11,130,133 B2
(45) Date of Patent: Sep. 28, 2021

(54) DEVICE AND METHOD FOR DETERMINING THE MIGRATION ABILITY OF AMOEBOIDALLY MOBILE CELLS

(71) Applicant: MEON MEDICAL SOLUTIONS GMBH & CO. KG, Graz (AT)

(72) Inventors: Herfried Huemer, Feldbach (AT); Doris Zahrl, Graz (AT); Horst Rüther, Hart/Graz (AT)

(73) Assignee: MEON MEDICAL SOLUTIONS GMBH & CO. KG, Graz (AT)

( * ) Notice: Subject to any disclaimer, the term of this patent is extended or adjusted under 35 U.S.C. 154(b) by 176 days.

(21) Appl. No.: 15/751,758

(22) PCT Filed: Aug. 9, 2016

(86) PCT No.: PCT/AT2016/050252
§ 371 (c)(1),
(2) Date: Feb. 9, 2018

(87) PCT Pub. No.: WO2017/024328
PCT Pub. Date: Feb. 16, 2017

(65) Prior Publication Data
US 2018/0229238 A1    Aug. 16, 2018

(30) Foreign Application Priority Data
Aug. 12, 2015  (EP) ..................... 15180818

(51) Int. Cl.
*B01L 3/00* (2006.01)
*C12M 3/00* (2006.01)
*G01N 33/50* (2006.01)

(52) U.S. Cl.
CPC .... *B01L 3/502761* (2013.01); *G01N 33/5091* (2013.01); *B01L 2200/0694* (2013.01);
(Continued)

(58) Field of Classification Search
CPC .............................. C12M 25/02; C12M 25/14
See application file for complete search history.

(56) References Cited

U.S. PATENT DOCUMENTS 5,284,753 A * 2/1994 Goodwin, Jr. ........ B01L 3/5025
435/288.4
6,350,610 B2  2/2002 Egger
(Continued)

FOREIGN PATENT DOCUMENTS

AT           394455       4/1992

OTHER PUBLICATIONS

English Abstract of AT394455.
(Continued)

*Primary Examiner* — Nathan A Bowers
(74) *Attorney, Agent, or Firm* — Dykema Gossett PLLC

(57) ABSTRACT

The invention relates to a migration device (100) having a sample chamber (102), a migration matrix (105) arranged in the sample chamber (102), and a fluid outlet (103). The migration device (100) also has a discharge structure (104), which is designed to discharge fluids from the sample chamber (102) to the fluid outlet (103). The invention also relates to methods for operating the migration device and to the use of a migration device for determining the migration ability of ameboidally mobile cells.

12 Claims, 6 Drawing Sheets

(52) U.S. Cl.
CPC . *B01L 2300/069* (2013.01); *B01L 2300/0681* (2013.01); *B01L 2300/0851* (2013.01); *B01L 2300/0858* (2013.01); *B01L 2300/0867* (2013.01); *B01L 2300/0874* (2013.01); *B01L 2400/049* (2013.01)

(56) References Cited

U.S. PATENT DOCUMENTS

| | | | |
|---|---|---|---|
| 2001/0004530 A1* | 6/2001 | Egger | B01L 3/5085 435/29 |
| 2003/0215941 A1* | 11/2003 | Campbell | B82Y 30/00 435/325 |
| 2007/0099294 A1* | 5/2007 | Yang | C12M 25/14 435/299.1 |
| 2007/0272000 A1* | 11/2007 | Kahl | B01L 3/502753 73/53.01 |
| 2011/0159522 A1* | 6/2011 | Kamm | C12Q 1/02 435/7.21 |
| 2012/0094325 A1* | 4/2012 | Irimia | B01L 3/502746 435/34 |
| 2013/0040334 A1* | 2/2013 | Kashanin | B01L 3/502753 435/29 |
| 2014/0178992 A1* | 6/2014 | Nakashima | C12N 5/0667 435/375 |
| 2016/0067710 A1* | 3/2016 | Larsen | G01N 1/4077 435/25 |
| 2016/0194588 A1 | 7/2016 | Guenat et al. | |

OTHER PUBLICATIONS

D.J. Barry et al., Nitrocellulose as a General Tool for Fungal Slide Mounts, J. Clinical Microbiology, vol. 45, No. 3, Mar. 2007, pp. 1074-1075.

\* cited by examiner

DEVICE AND METHOD FOR DETERMINING THE MIGRATION ABILITY OF AMOEBOIDALLY MOBILE CELLS

The invention relates to the determination of the migration ability of ameboidally mobile cells. In particular, the invention relates to a migration device for determining the migration ability of ameboidally mobile cells, the use of a migration device for determining the migration ability of ameboidally mobile cells, and a method for operating a migration device.

TECHNICAL BACKGROUND

The migration ability of ameboidally mobile cells can be determined by simulating the natural conditions in the body under standardised conditions outside the body, in vitro. Here, a porous membrane filter or a migration matrix of specific pore width and thickness replaces the tissue of the body and constitutes an artificial obstacle, which can be infiltrated for example by neutrophils. In this way, the readiness of the neutrophils to infiltrate the filter can be assessed under standardised conditions (filter quality, medium, time, irritants). The number and the distribution of the neutrophils that have infiltrated the filter can be measured and assessed.

A membrane filter system for measuring cell migration is described in AT 394 455 B. Said document presents a system that consists of a membrane filter to which a carrier matrix for test substances is attached on one side, which carrier matrix is in turn sealed off on the side opposite the membrane filter by an impermeable boundary layer. The solid test substances dissolve in the aqueous medium in which the cells to be examined are brought to the system from the membrane filter side, it being possible for the dissolution behaviour to be influenced by liberation stabilisers. The impermeable boundary layer forces the dissolved test substances to diffuse in the direction of the membrane filter, so as to influence the cell migration here. The migration ability is assessed on the basis of the number and distribution of cells in the membrane filter, these being determined by microscope.

To perform a migration measurement in vitro, a container ring is also secured to the membrane filter side of the system. A suspension of the cells to be tested is filled into the container ring. So as to then be able to assess the migration ability, it is necessary to remove the container ring from the membrane filter system and to secure the membrane filter system to an object carrier for the examination.

A similar device for measuring the migration ability of ameboidally mobile cells is described in AT 406 310 B and in US 2001/0004530 A1. The device is configured so that the area of the membrane filter is at least 1.6 times as large as the area of the base opening of the container ring. In the assembled state, a sufficient porosity of the region of the membrane filter resting between the lower end face of the container ring and the base surface thus remains, so that, once filled into the container ring, some of the non-cellular liquid phase flows into the region of the membrane filter disposed outside the base surface of the container. The cells are thus quickly brought into contact with the membrane filter.

In WO 2015/032 889 A1 a device for in-vitro modelling of living tissues and organs is described, wherein here cells are basically applied to culturing membranes and are cultivated there (for example lung cells) so as to thus perform examinations and studies. The 'culturing membranes' are arranged between chambers (access chambers or culturing chambers) which can be loaded by means of inflow channels and outflow channels with the substances required for the examinations. It is not possible to examine the migration of cells into a porous membrane with a device according to WO 2015/032 889 A1.

From D. J. BARRY et al: "Nitrocellulose as a General Tool for Fungal Slide Mounts", Journal of Clinical Microbiology, vol. 45, no. 3, 1 Mar. 2007, it is known to use membranes formed of nitrocellulose fixed in a frame in order to examine the growth of fungal cultures under a microscope in situ. After a growth phase, the membranes stained by immersion oil are made transparent and are examined under a microscope.

Definitions

Migration: Migration or cell migration (Latin: migrare, 'migrate') is understood to mean the active change in location (locomotion) of cells or cell structures. The umbrella term "migration" includes undirected spontaneous movement (random migration), directed chemotactic movement and a change in movement speed (chemokinetics).

Migration matrix: In the context of this application, a migration matrix is understood to mean a thin, preferably open-pore layer, into which ameboidally mobile cells can infiltrate (migrate), wherein the mean pore size of the migration matrix is preferably smaller than the mean diameter of the ameboidally mobile cells.

Ameboidally mobile cells: Ameboid movement describes a crawling movement of cells, for example as in amoeba, certain leukocytes, ameboid algae and some cancer cells.

SUMMARY OF THE INVENTION

The object of the invention can be considered that of simplifying the determination of the migration ability of ameboidally mobile cells.

This object is achieved by the subjects of the independent claims. Developments and embodiments can be found in the dependent claims, the description, and the drawings.

A first aspect of the invention relates to a migration device for determining the migration ability of ameboidally mobile cells. The migration device has a sample chamber, at least one migration matrix arranged in the sample chamber, at least one fluid outlet, and at least one discharge structure. The discharge structure is designed to discharge a fluid from the sample chamber and/or from the migration matrix.

A core concept of the invention can be considered that the migration device has a structure (discharge structure) designed to conduct a fluid out from the sample chamber. In this way, the use or operation of the migration device for determining the migration ability of ameboidally mobile cells can be simplified. For example, various liquids and/or gases (i.e. fluids) can be conducted away from the sample chamber by means of the discharge structure, and therefore the removal of these fluids from the sample chamber by means of a pipette or the like is unnecessary. This in turn allows the migration ability to be determined by means of the migration device in a more automated manner. Furthermore, the discharge structure can be designed to prevent the formation of air bubbles as the sample chamber is being filled. Further, the discharge structure can also be used to suck air through the sample chamber so as to bring about a drying process. All of these processes that are carried out by means of the discharge structure simplify the determination of the migration ability of ameboidally mobile cells by means of the migration device. In other words, the need for manual process steps when operating the migration device can be spared on account of the discharge structure, or the operation of the migration device can be limited to a few simple, uncritical movements performed by hand. Further advantages and applications of the migration device according to the invention will be described in the context of more detailed exemplary embodiments.

Many eukaryotic cells, such as fibroblasts, keratinocytes, neurons, immune cells, and amoebas, are capable of migration on account of amoeboid movement or active locomotion. The term "migration" or "cell migration" can be understood in the context of this invention to mean the active change in location of biological cells or cell structures capable of amoeboid movement. The umbrella term "migration" can include any active amoeboid cell movement, such as undirected active spontaneous movement (random migration), directed chemotactic movement (chemotaxis), and a change in the active movement speed (chemokinetics). The term "migratory performance" or "migration ability" or "migratory activity" can be understood in the context of this invention to mean active movement or the ability of ameboidally mobile cells to perform active movement.

A migration device, in the context of the invention, can be understood to mean a device that can be used for determining the migration ability of ameboidally mobile cells. The migration device can be formed so that it is configured for microscopy with a standard inverted microscope suitable for cell biology and/or for automatable manipulation steps, such as temperature control, washing, and staining.

In principle, the migration ability of any biological cell or cell structures capable of amoeboid movement can be determined using the device according to the invention. The migration device according to the invention can be used preferably for determining the migration ability of white blood cells (leukocytes), such as monocytes/macrophages, or of neutrophilic granulocytes (neutrophils). The migration device according to the invention can be used particularly preferably for determining, in-vitro, the migration ability of polymorphonuclear neutrophilic granulocytes (PMNs) from whole blood or from diluted whole blood as sample.

In the context of the invention, determining the migration ability can be understood to mean determining the in-vitro migration, measuring and/or assessing the migration or non-migration of ameboidally mobile cells. Here, the migration can be performed preferably by migration into a porous membrane filter or into a migration matrix, whereupon either the distribution of the cells in and on the membrane filter or the migration profile can be measured and assessed by microscope, once the migrated cells have been fixed and stained.

The migration device can have a housing, which can be made at least in part from plastic. This housing can contain the sample chamber, the fluid outlet, and the discharge structure. In other words, the sample chamber, the fluid outlet, and the discharge structure can be formed in the migration device or in the housing of the migration device.

The housing of the migration device can be formed here in one part or also in a number of parts, for example two parts. For example, the housing of the migration device can have an upper part and a lower part, which can be joined together or fitted together. The housing or the upper part and the lower part can be manufactured by means of injection moulding methods. The upper part and the lower part can each be formed in one piece.

The sample chamber, in the context of the invention, can be understood to mean an indentation or recess that is formed in the migration device or in the housing of the migration device. For example, the sample chamber can be an indentation or recess that is formed in the migration device or in the housing and that has a circular cross-section. However, the cross-section of the sample chamber can also have a different shape, for example an oval or rectangular shape. Furthermore, the sample chamber can have a side wall and a bottom surface, which will be discussed in further detail hereinafter. The sample chamber can be designed to perform therein the determination of the migration ability of ameboidally mobile cells. For example, a sample fluid can be introduced into the sample chamber so as to determine the migration ability of the ameboidally mobile cells contained in the sample liquid.

The sample chamber can have an inlet opening, through which fluids can be introduced into the sample chamber. This inlet opening can be closable. For example, the migration device can have a closure, for example a cover, for closing the inlet opening of the sample chamber.

The matrix, in the context of the present invention, can also be understood to be a membrane filter. A matrix of this kind or a membrane filter of this kind, which can be used in a migration device according to the present invention and can be part of the migration device, is described for example in AT 394 455 B. The membrane filter can receive the migrating cells. It can preferably contain carbohydrate compounds, such as cellulose derivatives (acetate, nitrate), polycarbonate, or those made of plastics, such as polyamide or polyvinyl chloride. The filters can be used without further preparation, or the inner walls of their pores can be coated with substances to which the migrating cells have certain affinities, such as collagen, fibrin, heteroglycans, or carbohydrate polymers, such as agar. The pore width of the membrane filter is based on the examined cell type and the objective of the examination. In the case of leukocytes, pore widths between 1 μm and 8 μm have proven to be advantageous. This specification is not to be understood as a limiting feature of the invention, since other pore widths can be more favourable depending on the cell type.

Furthermore, the matrix can also comprise a plurality of matrices. For example, the matrix can have two layers of first and second matrices arranged one above the other. The first matrix, for example, can be a migration matrix, and the second matrix, for example, can be a deposit matrix.

The second matrix or deposit matrix, in the context of the present invention, can also be a porous membrane filter containing one or more active substances. The deposit matrix can be a porous material into which an active substance can be incorporated in the solid state of matter and which dissolves upon contact with a sample liquid.

The matrix can lie on a bottom surface of the sample chamber. In the case that the matrix comprises a deposit matrix and a migration matrix, the deposit matrix can be arranged on the bottom surface of the sample chamber and the migration matrix can be arranged on the deposit matrix. In other words, as considered from top to bottom, the migration matrix can lie on the deposit matrix and the deposit matrix can lie on the bottom surface of the sample chamber. The deposit matrix can contain an active substance, wherein all substances that can exert a promoting or inhibitory effect on the migration of ameboidally mobile cells can be understood to be an active substance. Other active substances can also be contained. Depending on the objective, the deposit matrix can also contain no active substance or can also be dispensed with entirely.

For the deposit matrix, it is possible to use a porous membrane filter made of cellulose nitrate, and for the active substance it is possible to use the chemotactic tripeptide N-Formyl-methionyl-leucyl-phenylalanine (FMLP), which for example is introduced with agar into the deposit matrix. A deposit matrix of completely similar structure, but without active substance can be used as an empty control.

For example, the fluid outlet can be understood to mean an opening formed in the migration device or in the housing of the migration device, through which a fluid can be let out from the sample chamber. Here, the migration device can have one or more (for example two) fluid outlets separated from one another. The fluid outlet can be designed in such a way that a suction pump or a vacuum pump can be connected to the fluid outlet, so that fluids can be pumped out from the sample chamber and/or a negative pressure can be produced in the discharge structure. For example, the fluid outlet can have a sort of suction nipple, for example a Luer fitting, to which the suction pump or the vacuum pump can be attached. Both gases, for example air, and liquids, for example water, blood, etc., and also mixtures of gas and liquids can be understood as fluids in the context of the invention.

The discharge structure can be understood to mean a structure that is provided in the migration device or in the housing of the migration device and that is designed for discharging a fluid from the sample chamber and/or from the, or through the migration matrix to the fluid outlet. This discharge structure can be formed directly in the migration device or in the housing, for example in that one or more recesses is/are formed in the migration device or in the housing. The discharge structure can have one or more mechanical sub-structures. For example, the discharge structure can comprise additional components or elements, which are mounted on and/or secured to the migration device or the housing, for example additional tubes or channels. Furthermore, the discharge structure can comprise an outflow structure arranged on the sample chamber, for example an opening, a groove, a branched groove system, a grating structure, or another mechanical structure. In the context of the present invention the term "discharge structure" is used as a generic term for various embodiments of the fluid-mechanical connection between the sample chamber and the fluid outlet. A discharge structure thus provides a fluid-mechanical connection between the sample chamber and the fluid outlet. The discharge structure, in other words, can be designed to discharge fluids from the sample chamber to the fluid outlet. To this end, the migration device can produce a fluid connection between the discharge structure and the fluid outlet. The discharge of fluids by means of the discharge structure can be achieved for example in that the discharge structure is connected fluid-mechanically to a suction device, for example a pump.

Unless otherwise stated, a connection defined in the context of the present invention relates to a fluid connection. A fluid connection or a fluid-mechanical connection between two elements can be understood to mean that a connection (for example in the form of lines and/or channels) exists between the two elements, so that a fluid can flow from one of these elements to the other of these elements.

The discharge structure can comprise one or more individual structures separated from one another, which are each designed to discharge a fluid beyond the sample chamber and beyond the migration matrix, to the fluid outlet. For example, the discharge structure can have a first discharge structure and a second discharge structure. In other words, the discharge structure can be understood to mean the totality of all discharge structures designed to discharge a fluid beyond the sample chamber and beyond the migration matrix, to the fluid outlet. A discharge structure of this kind can be formed for example at least in part in the bottom surface and/or in the side wall of the sample chamber, wherein the discharge structure can also be arranged only in the bottom surface or only in the side wall. This means that the discharge structure can have a sub-structure, for example an outflow structure, formed in the bottom surface and/or in the side wall.

In order to record microscopic stack pattern images, either the camera used for this can be moved relative to the migration device or the migration device can be moved relative to the camera, on an x/y slide or over a circular path. In so doing, the camera can pass over a strip (circular path) with a width determined by the magnification factor, thus defining an optical path. In order to achieve uninhibited optical quality of the recorded images, the migration device can be constructed in such a way that the discharge structure is not guided through these optical paths, i.e. the optical paths are free from the geometric constructions of the discharge structures. The stack pattern images are recorded preferably through the base of the migration device, which has regions permeable for the measuring radiation.

In accordance with one exemplary embodiment of the invention, the migration device has a housing which contains the sample chamber or in which the sample chamber is formed. The discharge structure is also formed in the housing, and the discharge structure is designed to enable a fluid to be discharged beyond the housing.

Here, the housing can be formed in one part or in a number of parts. For example, the housing can have an upper part and a lower part, which in an assembled state of the migration device can be joined or fitted together. The housing for example can be made at least in part of plastic, for example by means of injection moulding methods. The plastic for example can be Eastman Tritan COPOLYESTER MX731. The advantages of this plastic are, inter alia: its high transparency; the prevention of streaks; its amorphous property; its high level of toughness; its good chemical compatibility upon contact with blood, in-vitro chemicals and immersion oil; its sterilisability (good colour resistance in the case of gamma or ethylene oxide (ETO) sterilisation); and its FDA/ISO 10993 and USP Class VI biocompatibility. The plastic of the housing can be selected for example so that, in combination with the adaptation of the refractive index of the migration index, an optical transparency of high microscopic quality can be achieved.

The housing can consist for example only of injection-moulded parts and/or of standard components which can be purchased. In this way, the migration device can be produced very economically.

In accordance with a further exemplary embodiment of the invention, the sample chamber has a bottom surface or a sub-base, wherein the migration matrix or the deposit matrix lies on the bottom surface and the discharge structure is formed at least in part in the bottom surface. This means that the discharge structure can have a mechanical sub-structure formed in the bottom surface, for example an outflow structure (for example in the form of a groove, a branched groove system, an opening, a grating, etc.).

The bottom surface of the sample chamber can be delimited for example by a side wall of the sample chamber. Furthermore, the bottom surface can be substantially flat or planar. The term "substantially" in this context can be understood to mean that the flat or planar bottom surface can have openings, indentations and/or recesses (for example the groove mentioned in the context of the invention). The bottom surface, however, for example can have a substantial part, for example more than 80% of the bottom surface, preferably more than 90% of the bottom surface, that is flat or planar apart from manufacturing tolerances. The bottom surface can alternatively also be curved. Furthermore, the bottom surface can also have a curved region and a planar region.

A discharge structure of this kind formed in the bottom surface of the sample chamber can also be referred to in the context of the invention as a first discharge structure. For example, the discharge structure formed in the bottom surface can comprise, at least in part, a groove arranged in the bottom surface. The discharge structure formed in the bottom surface can also comprise a spacer lattice, which is arranged between the migration matrix and the bottom surface. Furthermore, the discharge structure formed in the bottom surface can have a bore or a plurality of bores, for example continuous channel-like holes, which are formed in the bottom surface of the discharge structure and which are combined in the migration device or in the housing of the migration device in a channel.

The discharge structure can be formed in such a way that the matrix (migration or deposit matrix) lies on the bottom surface and at least in part on the discharge structure. This means that the discharge structure can be arranged beneath the matrix of the migration device and/or is covered thereby. By means of a discharge structure of this kind arranged in the bottom surface of the sample chamber, it is possible for gas bubbles, which form between the matrix and the bottom surface, to be effectively removed. Furthermore, fluids can also be discharged from the sample chamber through the migration matrix in this way. For example, an effective drying process can be brought about in this way, in that air is sucked from the sample chamber and through the matrix by means of the discharge structure arranged in the bottom surface, so that the matrix is also effectively dried.

In accordance with a further exemplary embodiment of the invention the discharge structure formed in the bottom surface has a groove arranged in the bottom surface.

In the context of the invention the groove can also be referred to as a (upwardly open) discharge channel. This groove for example can open out into a channel formed in the migration device, which channel connects the groove to the fluid outlet. Thus, a fluid-tight connection can be provided between the groove and the fluid outlet. The groove for example can run from the middle of the bottom surface of the sample chamber to the edge of the bottom surface of the sample chamber. For example, the groove can have a length of from approximately 4 mm to 15 mm, a width of from approximately 0.5 mm to 1 mm, and a depth of from approximately 0.5 mm to 1 mm. These dimensions of the groove can be oriented towards the dimensions of the migration area (base) and/or the effective cross-section thereof, which is defined by the structural design. The diameter of the migration area can be approximately 3 mm to 10 mm, and that of the migration area together with clamping region approximately 5 mm to 20 mm.

In this way, a structure can be provided that prevents the formation of gas bubbles and makes it possible to discharge fluids.

In accordance with a further exemplary embodiment of the invention the discharge structure has a first fluid channel arranged in the migration device and passing from the sample chamber to the fluid outlet.

For example the fluid channel can enable a fluid-tight connection between the fluid outlet and an opening in a bottom surface of the sample chamber and/or in a side wall of the sample chamber.

In accordance with a further exemplary embodiment of the invention the sample chamber comprises a side wall. Furthermore, the discharge structure comprises an opening arranged in the side wall of the sample chamber for suction of fluids from the sample chamber. In addition, the discharge structure has an annular fluid channel, which is arranged in the migration device around the sample chamber. The discharge structure has a fluid connection between the annular fluid channel and the fluid outlet. This fluid connection can be provided for example by the first fluid channel. The discharge structure also has a fluid connection between the opening arranged in the side wall and the annular fluid channel.

In other words, the discharge structure can have a fluid channel which surrounds the sample chamber, for example annularly. This annular fluid channel for example can be connected fluid-mechanically to an opening arranged in the bottom surface of the sample chamber, for example a groove. Furthermore, the fluid channel can also be connected to the opening or to openings that is or are arranged in a side wall of the sample chamber. For example, the annular channel can combine a plurality of openings, which can be formed both in the side wall and in the bottom surface of the sample chamber, so as to form a single fluid channel, for example the previously defined first fluid channel, so that fluids can be conducted or discharged both from the openings in the side wall and from the openings in the bottom surface of the sample chamber to the fluid outlet.

This opening or these openings formed in the side wall of the sample chamber can also be referred to as a second discharge structure. Fluids can be discharged from above the migration matrix by means of this opening formed in the side wall. This discharge can be used for example for the fixing, washing, staining and/or drying for the determination of the migration ability. These openings formed in the side wall can also be referred to hereinafter as clamping ring orifices.

In accordance with a further exemplary embodiment of the invention the sample chamber has a bottom surface and a side wall, wherein the matrix (migration or deposit matrix) lies on the bottom surface. The discharge structure is formed at least in part in the bottom surface, for example in the form of a groove. Furthermore, the discharge structure has an opening arranged in the side wall of the sample chamber. Here, the discharge structure formed in the bottom surface and the opening arranged in the side wall are connected to the same fluid outlet. The discharge structure formed in the bottom surface and the opening arranged in the side wall are connected either in series or in parallel with regard to their fluid connection. The migration device can have a single opening or a plurality of openings in the side wall of the sample chamber.

In other words, a first discharge structure and a second discharge structure can be connected or arranged in series or in parallel in terms of their fluid connection to the fluid outlet. The advantage of a series connection of the first discharge structure and of the second discharge structure relative to one another lies, inter alia, in that fluids that are discharged through the discharge structure arranged at the front in the series connection are also conducted through the discharge structure arranged subsequently in the series connection, so that the subsequent discharge structure is cleaned when fluids are flushed through it.

In the case of an arrangement in series, the differential pressure between the upper side and underside of the matrix can be set differently, by closer coupling, by means of the flow rate, so that a reproducible fluid transport through the matrix is generated. Washing, staining and drying processes can be carried out more quickly and more uniformly alongside a reduced reagent consumption.

In the case of a series connection or connection in series of the discharge structure formed in the bottom surface and of the openings arranged in the side wall, the discharge structure formed in the bottom surface and the openings arranged in the side wall can be arranged in succession with regard to their fluid connection. This means that the fluid outlet for example can be directly connected to the discharge structure in the bottom surface and that the discharge structure formed in the bottom surface can be directly connected to the opening arranged in the side wall. Alternatively, the fluid outlet can be directly connected to the opening arranged in the side wall, and the opening arranged in the side wall can be directly connected to the discharge structure in the bottom surface. In the case of a parallel connection of the discharge structure formed in the bottom surface and of the opening arranged in the side wall to the fluid outlet, the discharge structure formed in the bottom surface and the opening arranged in the side wall can each be directly connected to the fluid outlet, separately. However, this does not rule out the fact that the discharge structure formed in the bottom surface and the opening arranged in the side wall are separately connected to the same fluid channel (for example referred to as the first fluid channel within the context of the invention), which connects the fluid outlet to the two openings.

Both in the series connection and in the parallel connection of the discharge structure formed in the bottom surface and of the openings arranged in the side wall, the two openings can be connected to the same fluid outlet. This has the advantage that a single suction pump or vacuum pump is sufficient to discharge fluids from the sample chamber by means of the opening arranged in the bottom surface and the opening arranged in the side wall.

In accordance with a further exemplary embodiment of the invention the sample chamber comprises a bottom surface and a side wall. The discharge structure also has a discharge structure formed in the bottom surface and an opening arranged in the side wall. The migration device also has at least two separate fluid outlets or two fluid outlets separated from one another, wherein the discharge structure formed in the bottom surface and the opening arranged in the side wall are connected to two separate fluid outlets.

In other words, the discharge structure formed in the bottom surface can be connected to a first fluid outlet and the opening arranged in the side wall can be connected to a second fluid outlet.

The advantage resulting from the fact that the discharge structure formed in the bottom surface and the opening arranged in the side wall are connected to separate fluid outlets is that the outflows through the discharge structure formed in the bottom surface and through the opening arranged in the side wall can be separately managed or controlled.

In accordance with a further exemplary embodiment of the invention the migration device has an upper part which has a through-opening, which is spatially delimited from a side wall, and a first receiving region or receiving area. Furthermore, the migration device has a lower part, which has a second receiving region or receiving area. The upper part and the lower part can be joined together in an assembled state of the migration device. In the assembled state of the migration device the migration matrix is arranged in the first receiving region and in the second receiving region. The through-opening together with the side wall forms the sample chamber, and the lower part forms a base of the sample chamber, wherein the matrix lies on the base. Furthermore, at least the lower part has the discharge structure.

In accordance with a further exemplary embodiment of the invention, the discharge structure comprises a groove arranged in the lower part, wherein the groove is arranged at least in part in the second receiving region, so that the groove in the assembled state of the migration device is covered by the matrix (migration or deposit matrix).

In accordance with a further exemplary embodiment of the invention the upper part and the lower part are designed to fix the matrix in a specific region of the matrix between the first receiving region of the upper part and the second receiving region of the lower part.

In accordance with a further embodiment of the invention the first receiving region is embodied as a clamping ring, which surrounds an opening of the through-opening. Furthermore, the first receiving region is also designed to receive the matrix, which covers the opening of the through-hole and forms the base of the sample chamber.

In accordance with a further exemplary embodiment of the invention the upper part has an annular fluid channel, which surrounds the clamping ring. The upper part also has a fluid outlet with a connection piece for connecting a vacuum pump to the fluid outlet. The upper part also has a further fluid channel, which provides a fluid-tight connection between the fluid outlet and the annular fluid channel.

In other words the housing of the migration device can be constructed in two parts, i.e. from the upper part and the lower part. The first and the second receiving region can each denote a region of the upper part and of the lower part respectively, between which the migration matrix is fixed in the assembled state. The second receiving region, which is formed in the lower part, can be a flat or planar surface, which in the assembled state of the migration device forms the bottom surface of the sample chamber. The first receiving region, which is formed in the upper part, can be a clamping ring surrounding the sample chamber, so that the migration matrix and as applicable the deposit matrix is fixed between the bottom surface (i.e. the second receiving region) and the clamping ring (i.e. the first receiving region).

The advantage of a two-part design of this kind lies, inter alia, in the fact that the matrix can be easily fixed between the upper part and the lower part.

A further aspect of the invention relates to the use of a migration device according to any one of the preceding claims for determining the migration ability of ameboidally mobile cells.

A further aspect of the invention relates to a method for operating a migration device which comprises the step of providing a migration device having a sample chamber, a migration matrix, and a discharge structure for discharging a fluid from the migration device to a fluid outlet of the migration device. Furthermore, the method comprises the step of discharging a fluid beyond the sample chamber and beyond the migration matrix, through the discharge structure, to the fluid outlet.

The method can also comprise the step of providing a migration device as described within the context of the invention. Here, the provided migration device can have some or all of the features described within the context of the invention.

In accordance with an exemplary embodiment of the invention a method for removing a sample or a treatment liquid is described. The method comprises the step of introducing the sample or the treatment liquid into the sample chamber. The step of discharging a fluid comprises a discharge of at least some of the sample or at least some of the treatment liquid through the discharge structure.

In accordance with a further exemplary embodiment of the invention a method for rinsing the migration device is described, which additionally comprises the step of introducing a rinsing liquid into the sample chamber. The step of discharging a fluid comprises a discharge of at least some of the rinsing liquid through the discharge structure.

In accordance with a further exemplary embodiment of the invention a method for drying the migration device is described, which additionally comprises the step of introducing air through an inlet opening of the migration device into the sample chamber by suction, through the discharge structure. The step of discharging a fluid to the fluid outlet comprises a discharge of the sucked air through the discharge structure.

The sample chamber can have an inlet opening, through which fluids can be introduced into the sample chamber. In other words, the inlet opening can be understood to mean an upper opening of the sample chamber. This inlet opening can be closable, for example. This means that the migration device can have a cover for closing the inlet opening.

In accordance with a further exemplary embodiment of the invention a method for preparing a migration device for an optical examination of the migration matrix is described, which method additionally comprises the steps of introducing a liquid into the matrix, wherein the introduced liquid, for example an immersion oil, has substantially the same refractive index as the matrix material, whereby the matrix is transparent. The liquid can be introduced by inserting a needle through an inlet opening of the migration device into the migration matrix, wherein the needle penetrates through the matrix and at least in part into the discharge structure.

In accordance with a further exemplary embodiment of the invention a method for migration analysis is described, which comprises the steps of introducing a sample liquid into the sample chamber, of fixing cells of the sample liquid by introducing a fixing liquid, of staining the cells by introducing a staining liquid into the sample chamber, and of optically measuring a migration ability of the cells, wherein all steps of this method are carried out using the migration device. Here, it can be understood that all steps of the method are carried out within or by means of the migration device.

The method steps described in the context of the invention, unless specified otherwise, can be carried out both in the described order and in other orders. Furthermore, the methods according to the invention or steps thereof can be carried out using the migration device described in the context of the invention. The described embodiments relate equally to a migration device, the use of a migration device, and methods for operating the migration device. Synergistic effects can result from various combinations of the embodiments, although these might not be described explicitly hereinafter. Features that characterise the device can also characterise the method for operating the device. Conversely, features that define how the device should be operated can, themselves, also be features of the device.

Further features, advantages and possible applications of the invention will become clear from the following description of the exemplary embodiments and drawings. Here, all features described and/or shown in the drawings also form the subject matter of the invention individually and in any combination, regardless of their formulation in the individual claims and the dependency references of the claims.

The drawings have been shown schematically and are not necessarily to scale. Should elements be denoted by like reference signs in different drawings, these thus denote like or similar elements or elements corresponding to one another. However, like or similar elements, or elements corresponding to one another can also be denoted differently in different drawings.

DETAILED DESCRIPTION OF EXEMPLARY EMBODIMENTS

Figure 1:
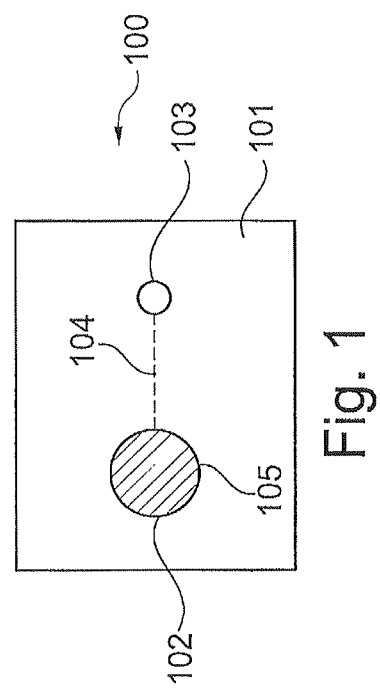
FIG. 1 shows a plan view of a migration device in accordance with an exemplary embodiment of the invention.

FIG. 1 shows a migration device 100, in simplified form, which has a housing 101. The migration device 100 also contains a sample chamber or migration chamber 102, which is formed in the housing 101 of the migration device 100. In accordance with this exemplary embodiment, the sample chamber 102 is formed as a circular indentation or recess in the housing 101. However, the sample chamber 102 can also have a different cross-sectional shape. Furthermore, the migration device 100 contains a migration matrix 105, which is arranged in the sample chamber 102. In addition, the migration device 100 has a fluid outlet 103. The migration device 100 also has a discharge structure 104, which is designed to discharge a fluid beyond the sample chamber 102 and beyond the migration matrix 105, to the fluid outlet 103. In other words, the discharge structure 104 produces a fluid connection between the sample chamber 102 and the fluid outlet 103, so that fluids can be discharged from the sample chamber 102 to the fluid outlet 103.

Figure 2:
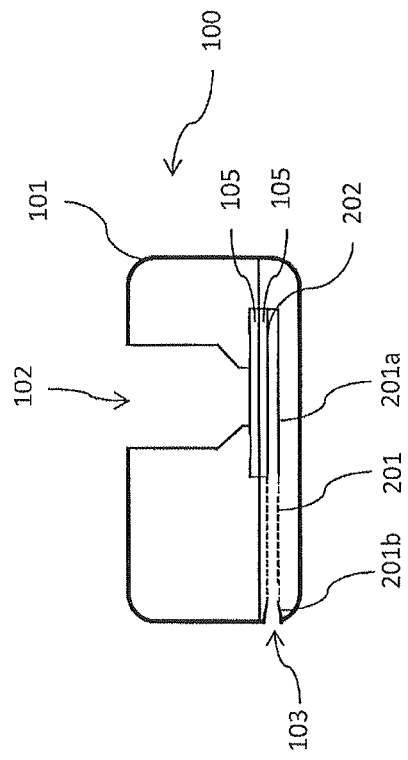
FIG. 2 shows a side view of a migration device in accordance with a further exemplary embodiment of the invention.

FIG. 2 shows a migration device 100 in accordance with a further exemplary embodiment of the invention, which migration device contains a housing 101 having a sample chamber 102 and a fluid outlet 103. In this exemplary embodiment the upper opening of the sample chamber 102 is the inlet opening of the sample chamber 102 described within the context of the invention. The migration matrix 105 is arranged on the base 202 of the sample chamber so that it lies on the base 202 of the sample chamber. Furthermore, the discharge structure 201 is formed at least in part in the base 202 of the sample chamber 102 so that the discharge structure formed in the base 202 is covered at least in part by the migration matrix 105. For example, the discharge structure 201 comprises an outflow structure 201*a* formed in the base, for example an opening, groove or groove system formed in the base. The discharge structure 201 also comprises an outlet opening 201*b*. Furthermore, the discharge structure 201 has a first fluid channel, which leads from the outflow structure 201*a* formed in the base to the outlet opening 201*b* or the fluid outlet 103. In this way, fluids that are discharged from the sample chamber 102 through the discharge structure 201 to the fluid outlet 103 are conducted through the migration matrix 105. The discharge structure 201 shown by way of example in FIG. 2 can also be referred to in the context of the invention as a first discharge structure.

Figure 3:
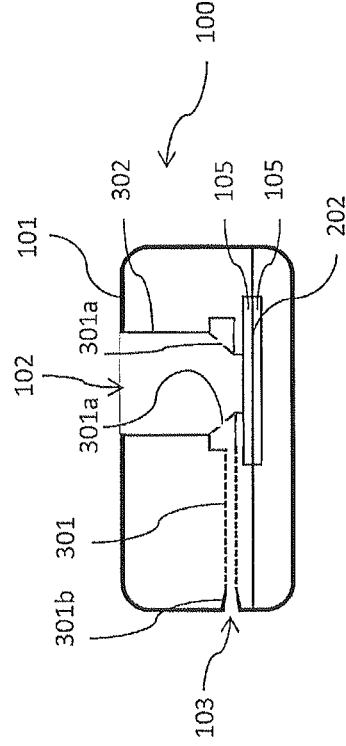
FIG. 3 shows a side view of a migration device in accordance with a further exemplary embodiment of the invention.

FIG. 3 shows a migration device 100 in accordance with a further exemplary embodiment of the invention. The migration device 100 has a housing 101 with a sample chamber 102, a migration matrix 105, and a fluid outlet 103. The discharge structure 301 of the migration device 100 according to FIG. 3 is formed in such a way that it leads from the side wall 302 of the sample chamber to the fluid outlet 103. This means that the discharge structure 301 opens out into the side wall 302 of the sample chamber 102. In other words, the discharge structure 301 has one or more openings 301*a* formed in the side wall of the sample chamber 102. Furthermore, the discharge structure 301 has a fluid channel, which leads from the openings 301*a* formed in the side wall to the outlet opening 301*b*. In this way, fluids that are discharged from the sample chamber 102 to the fluid outlet 103 do not have to be conducted through the migration matrix 105. The discharge structure 301 shown by way of example in FIG. 3 can also be referred to within the context of the invention as a second discharge structure.

Figure 4:
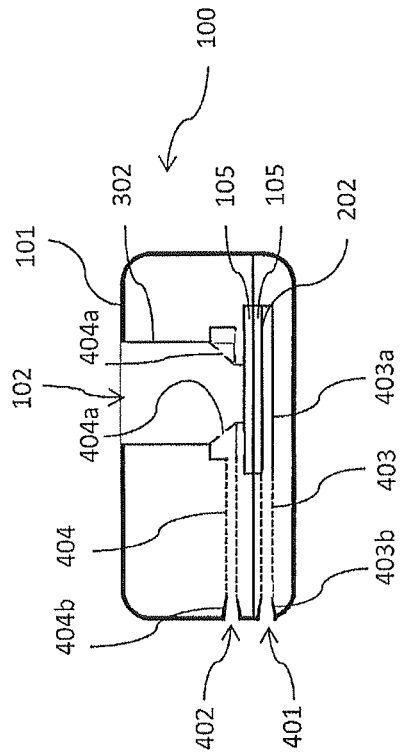
FIG. 4 shows a side view of a migration device in accordance with a further exemplary embodiment of the invention.

FIG. 4 shows a migration device 100 in accordance with a further exemplary embodiment of the invention. The migration device 100 has a housing 101 with a sample chamber 102, a migration matrix 105, a first fluid outlet 401, and a second fluid outlet 402. The discharge structure comprises a first discharge structure 403 and a second discharge structure 404. The first discharge structure 403 is formed in such a way that fluids are discharged from the bottom surface 202 of the sample chamber 102, through the first discharge structure 403, to the first fluid outlet 401. The first discharge structure 403 comprises an outflow structure 403*a* formed in the base, a first fluid channel, and a first outlet opening 403*b*. In this way, fluids that are discharged through the discharge structure 403 are conducted through the migration matrix 105. The second discharge structure 404 is formed in such a way that fluids are discharged from the sample chamber 102 from the side wall 302, through the second discharge structure 404, to the second fluid outlet 402. The second discharge structure 404 comprises one or more openings 404*a* formed in the side wall, a second fluid channel, and a second outlet opening 404*b*. In this exemplary embodiment it is shown that the first discharge structure 403 and the second discharge structure 404 are connected to separate fluid outlets 401 and 402. However, the first discharge structure 403 and the second discharge structure 404 can also be connected to the same fluid outlet and can be connected in series or in parallel.

Figure 5A:
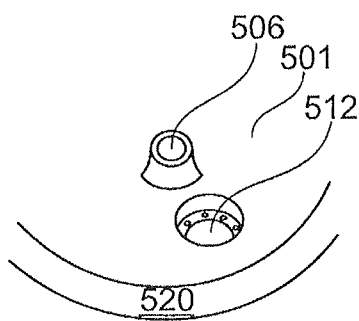
FIG. 5A, FIG. 5B, FIG. 5C and FIG. 5D show various views of a migration device in accordance with a further exemplary embodiment of the invention.
Figure 5B:
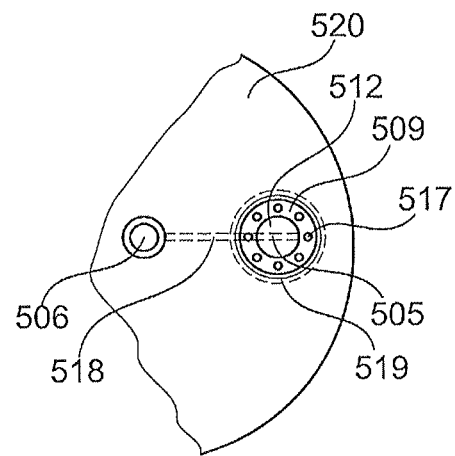
Figure 5C:
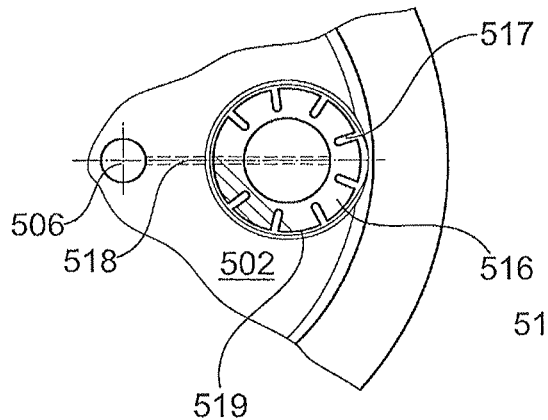
Figure 5D:
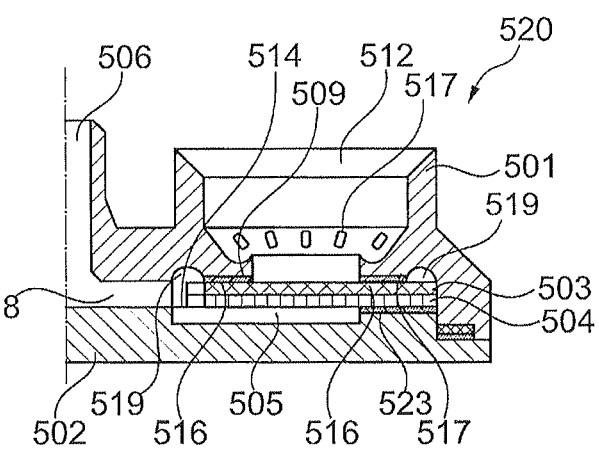

FIG. 5A, FIG. 5B, FIG. 5C and FIG. 5D show various views of a migration device in accordance with a further exemplary embodiment of the invention. The housing of the migration device here has an upper part 501 and a lower part 502. In FIG. 5A the upper part 501 is shown in a 3D view. FIG. 5B shows the upper part and the lower part in a plan view. FIG. 5C shows the lower part and the matrix arranged thereon after the stamping process. FIG. 5D shows a sectional view of the migration device 250.

As shown in FIG. 5D, the migration device 520 has an upper part 501 and a lower part 502, between which the matrix 503, 504 is arranged or fixed. In this exemplary embodiment the matrix comprises two layer-like matrices 503 and 504 arranged one above the other, wherein the upper matrix is a migration matrix 503 and the lower matrix is a deposit matrix 504. The upper part 501 also comprises the fluid outlet 506, which has a central suction connector or suction nipple, for example a Luer fitting. Furthermore, the upper part 501 contains a through-opening which forms the sample chamber 512. The upper opening of the sample chamber 512 in this exemplary embodiment forms the inlet opening of the sample chamber 512. The upper part 501 also has a first receiving area or region, which is formed as a clamping ring 509 or annular clamping region. The lower part 502 comprises a second receiving area or region 523, so that the matrices 503, 504 are fixed in a clamping region 516 between the first receiving region 509 (that is to say the clamping ring) and the second receiving region 523. The clamping region 516 forms a suction path, which will be described hereinafter. Since the lower part 502, as will be explained further below, has a groove 505 or a groove system, the second receiving region 523 can be interrupted by the groove 505.

The migration device 520 also has a discharge structure, which comprises a plurality of individual sub-structures. Inter alia, the discharge structure has a groove 505 formed in the bottom surface of the lower part 502, an annular fluid channel 519, which surrounds the sample chamber 512 annularly, formed in the upper part, a first fluid channel 518, and a plurality of openings 517 arranged in the side wall of the sample chamber 512, which openings are fluid-mechanically connected to the annular fluid channel 519. Hereinafter, the groove 505 can also be referred to as a suction or discharge channel. The annular fluid channel 519 can also be referred to as a ring channel, and the openings 517 arranged in the side wall can also be referred to as clamping ring orifices. The annular fluid channel 519 and the groove 505 are connected to one another at the connection point 514. The groove 505 formed in the bottom surface of the lower part 502 is fluidically connected to the annular channel 519, which is in turn fluidically connected to the first fluid channel 518, which is in turn fluidically connected to the fluid outlet 506.

The migration device comprises a migration matrix 503 with a pore width suitable for the migration and a deposit matrix 504 for receiving an active substance. The two matrices 503, 504 are pressed by the clamping region or clamping ring 509 of the upper part 501 against the receiving region 523 of the lower part 502 with a pressure that is of such a magnitude that a sufficient tightness is achieved over the entire periphery of the clamping region, but at the same time there is still sufficient porosity in the matrix portions 503, 504 beneath the clamping ring 509 to define a capillary creep path or suction path for the sample in the clamping region 516 between the sample chamber 512 and the annular channel 519.

The discharge structure has a first discharge structure arranged beneath the matrices in the base, for example a narrow suction channel or a groove 505, or a branched groove system, which is connected to the ring channel 519 and to the first fluid channel 518 so as to enable a transport of fluid (for example of the sample liquid, air, reagents, immersion oil, etc.) through the two matrices 503, 504 and thus so as to allow a quick and effective material exchange or so as to prevent a build-up of air and formation of air bubbles (see 522) at the time of first wetting. When connecting an air pump (for example suction pump, vacuum pump) to the suction nipple of the fluid outlet 506, the main part of the sample chamber 512 filled for example with a reagent or washing solution is emptied via the clamping ring orifices 517, annular channel 519 and first fluid channel 518 in the presence of a sufficient negative pressure.

Figure 5E:
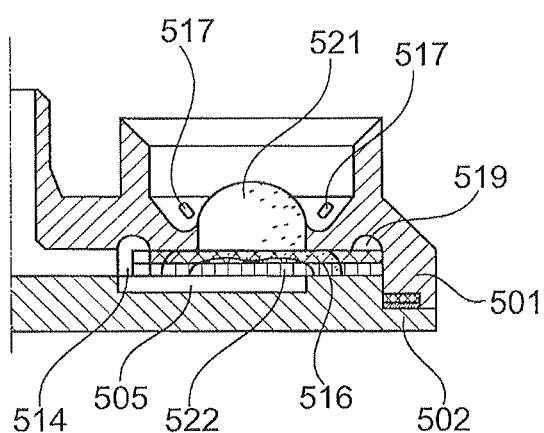
FIG. 5E and FIG. 5F each show a migration device in accordance with an exemplary embodiment of the invention during operation of the migration device.

FIG. 5E shows the first wetting of the migration matrix in the migration device shown in FIG. 5A to FIG. 5D in accordance with the exemplary embodiment of the invention. The sample, for example whole blood, is diluted with a buffer prior to being applied to the migration matrix 503. Some of the aqueous component of the sample quickly passes through the migration and deposit matrices 503, 504 and dissolves the active substance in the deposit matrix 504. This results in an active substance gradient for the cells in the sample that are to be analysed. By suitable selection of a carrier material, the release kinetics of the active substance can be controlled so as to thus maintain the gradient for a specific time.

It has proven to be advantageous to perform a pre-wetting of the matrices 503, 504 with a buffer. The diluted sample is then applied to the migration matrix 503. In accordance with a predetermined incubation time (typically 15 to 30 minutes), the migration process is stopped by fixing the cells, for example by formaldehyde. A single-stage or multi-stage process is then performed, in which the cells or cell components are stained. In order to achieve optical transparency, the air is forced from the pores of the matrices by use of a liquid 515 (for example immersion oil) having an appropriate refractive index and the migration paths of the cells are determined by means of an optical analysis (for example microscopic images). The optical analysis is preferably performed through the base of the device, which is optically permeable or transparent at least in regions.

The first discharge structure formed beneath the deposit matrix in the lower part 502 makes it possible for gases and air bubbles to escape quickly, for example in the form of a suction channel (for example groove 505, groove system or grating structure), and makes it possible for the matrices 503, 504 to be dried quickly and efficiently.

In order to ensure a reproducible process and to prevent drying out, a constant temperature, for example 37° C., and a high humidity can be necessary during the incubation. This is achieved advantageously in that the sample chambers 512 of the migration device 520 are made relatively small and are closed and temperature-controlled from the top and bottom sides during the incubation period.

Fixing and staining processes are facilitated, accelerated and improved in terms of quality by an outflow beneath the matrices, for example in the form of the groove 505, merely by application of a sufficient flow and the resultant negative pressure, without additional bores, channels, valves, etc., so that a significant amount of time can be saved in the case of repeated sub-steps, since the fluid exchange (reagents) and the drying process (air) is not provided exclusively by diffusion, but instead can be provided in a time-saving and more complete manner by convection.

Furthermore, intermediate washing processes metered drop by drop have proven to be advantageous, since the efficiency of the washing can be increased by the alternate suction of air and water under negative pressure.

Figure 5F:
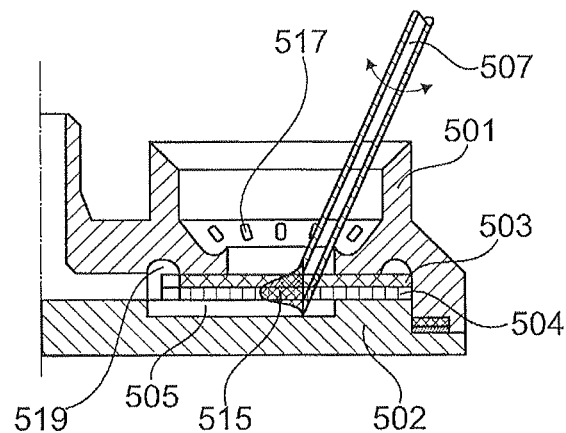

FIG. 5F shows the introduction of a liquid, for example of an immersion oil, into the migration matrix. The introduction of the immersion oil 515 can be associated with the risk that the immersion oil 515 applied to the migration matrix 503 penetrates the matrix in a time-delayed manner on account of the increased viscosity of said immersion oil and the areas of the surface that can be differently wetted locally due to the prior fluid processes or also due to the production process, and that the air displaced from the matrices 503, 504 by the fluid front cannot escape upwardly or outwardly, and as a result air bubbles of larger or smaller size thus accumulate beneath the deposit matrix 504 and/or between the two matrices 503, 504. This effect can become intensified if the pore width of the deposit matrix 504 is smaller than that of the migration matrix 503. The pore width of the deposit matrix is usually smaller so as to provide the greatest surface possible for the delivery of the attractant. It is therefore advantageous to introduce the immersion oil 515 using a needle 507 that tapers, for example an injection needle, in that the tapering part of the needle tip penetrates both matrices in the region of the groove 505 of the sub-base and at the same time can infiltrate the reagent laterally in and beneath both matrices. This process can be improved further still by turning the needle as it is introduced and/or by applying negative pressure at the same time at the groove 505.

Figure 6:
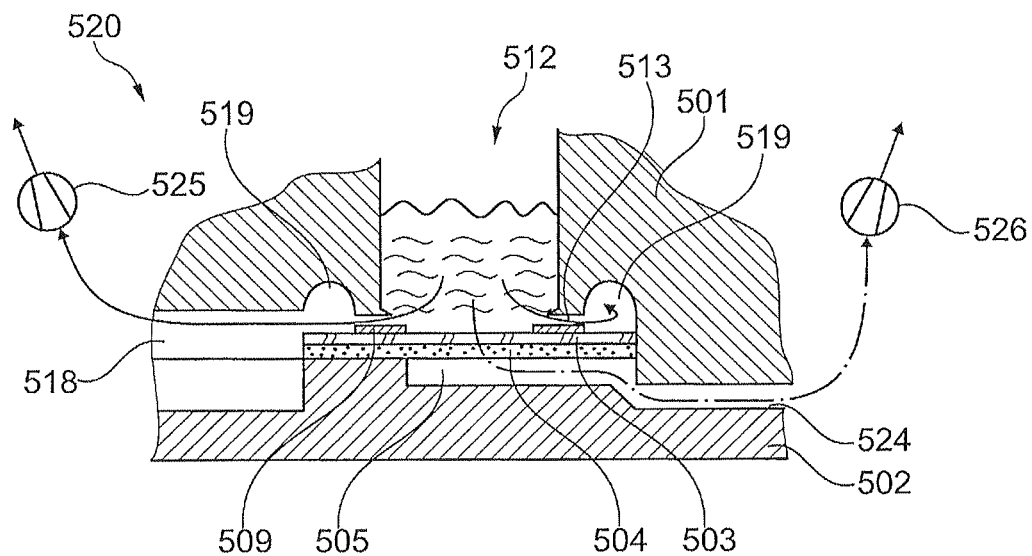
FIG. 6 shows a migration device with two discharge structures that are connected to different fluid outlets, in accordance with a further exemplary embodiment of the invention.

FIG. 6 shows a migration device 520 in accordance with a further exemplary embodiment of the invention. The migration device has an upper part 501 and a lower part 502. The sample chamber 512 is formed in the upper part, with the migration matrix 503 and the deposit matrix 504 arranged on the base of said sample chamber and fixed between the clamping ring 509 of the upper part 501 and the lower part 502. On the whole, the migration device has a discharge structure that contains a groove 505 formed in the lower part and openings 513 formed in the side wall of the sample chamber. The openings 513 formed in the side wall are connected by means of the annular channel 519 to the first fluid channel 518 and thus to a first suction pump or vacuum pump 525. The groove 505 formed in the lower part is connected by means of a second fluid channel 524 to a second fluid outlet and a second vacuum pump 526. This means that the groove 505 arranged beneath the migration matrix 503 and deposit matrix 504 is connected to a different fluid outlet compared to the openings 513 formed in the side wall, and therefore the flows through the groove 505 and through the openings 513 formed in the side wall can be controlled separately.

Figure 7:
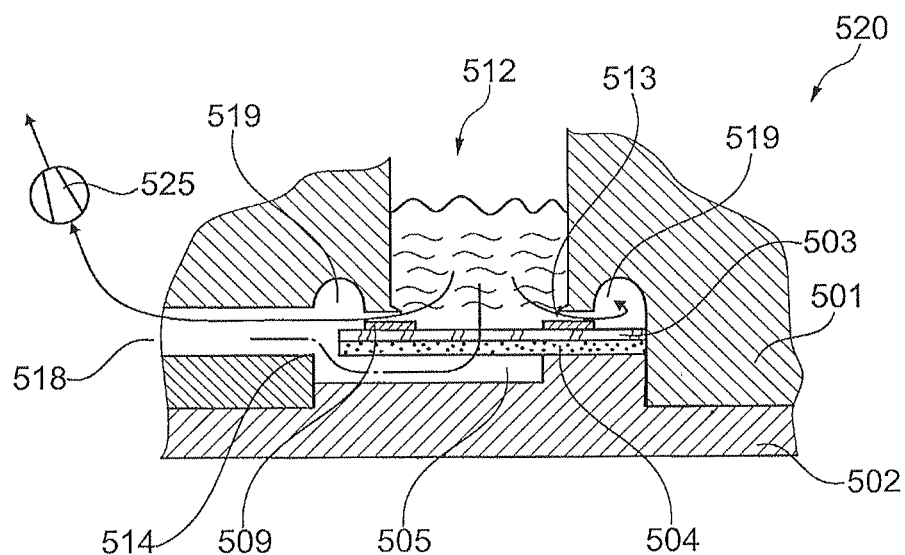
FIG. 7 shows a migration device with two discharge structures that are connected to the same fluid outlet and that are connected in parallel, in accordance with a further exemplary embodiment of the invention.

FIG. 7 shows a migration device 520 in accordance with a further exemplary embodiment of the invention, which migration device likewise has an upper part 501 and a lower part 502. The sample chamber 512 is formed in the upper part 501. The migration matrix 503 and the deposit matrix 504 are fixed between the clamping ring 509 of the upper part and the lower part 502, which forms the base of the sample chamber. The discharge structure has a groove 505 formed in the lower part, openings 513 formed in the side wall of the sample chamber 512, an annular channel 519, and a fluid channel 518. Here, the openings 513 arranged in the side wall and the groove 505 formed in the lower part 502 are connected to the same fluid channel 518 and thus to the same suction pump or vacuum pump 525. The groove 505 is connected here to the fluid channel 518 by means of the connection point 514. In accordance with this exemplary embodiment the groove 505 and the openings 513 formed in the side wall are fluidically connected in parallel. This means that the groove 505 and the openings 513 formed in the side wall are connected separately to the fluid channel 518.

Figure 8:
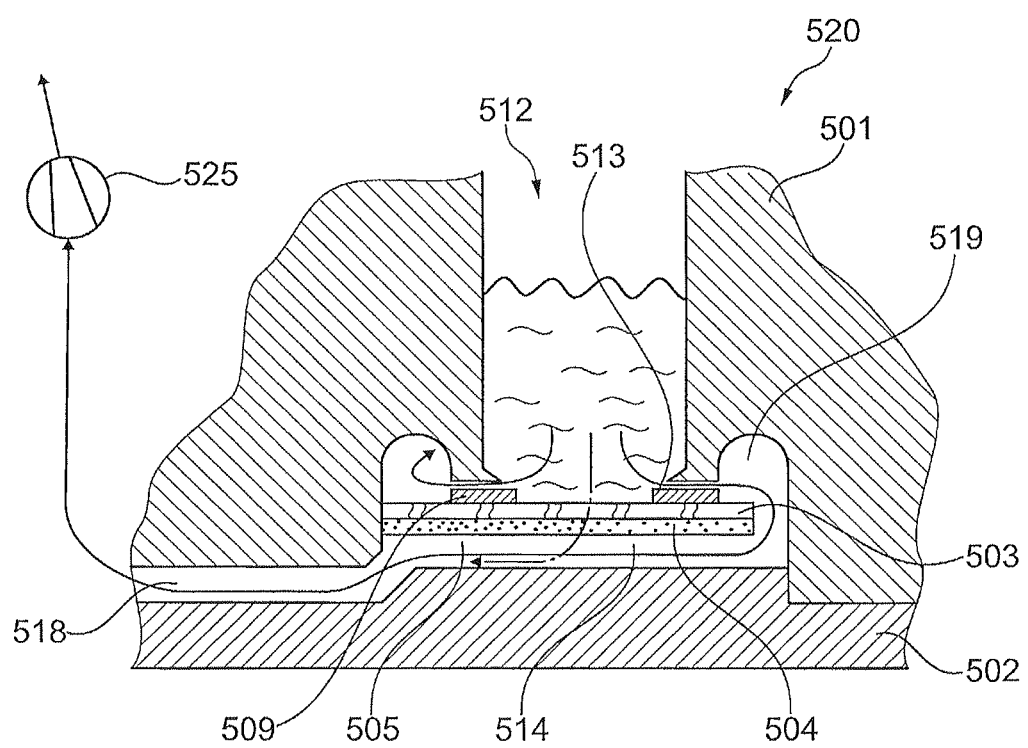
FIG. 8 shows a migration device with two discharge structures that are connected to the same fluid outlet and that are connected in series, in accordance with a further exemplary embodiment of the invention.

A migration device 520 is shown in FIG. 8 which has an upper part 501 and a lower part 502, wherein the upper part contains the sample chamber 512. The migration matrix 503 and the deposit matrix 504 are fixed between the clamping ring 509 of the upper part 501 and the lower part 502. The discharge structure has a groove 505 formed in the lower part, an annular channel 519, openings 513 formed in the side wall, and a fluid channel 518, which in terms of their fluid connection are connected in series and are provided with the suction pump or vacuum pump 525. The fluid channel 518 is connected fluid-mechanically to the groove 505, the groove 505 is connected fluid-mechanically to the annular channel 519, and the annular channel is connected fluid-mechanically to the sample chamber 512 by means of the openings 513 formed in the side wall. This means that fluids that are discharged through the openings 513 formed in the side wall are conducted through the groove 505. This in turn has the advantage that the groove 505 is rinsed by the liquid that is flushed through the groove 505 when said liquid is sucked through the openings 513 of the side wall.

Figure 9:
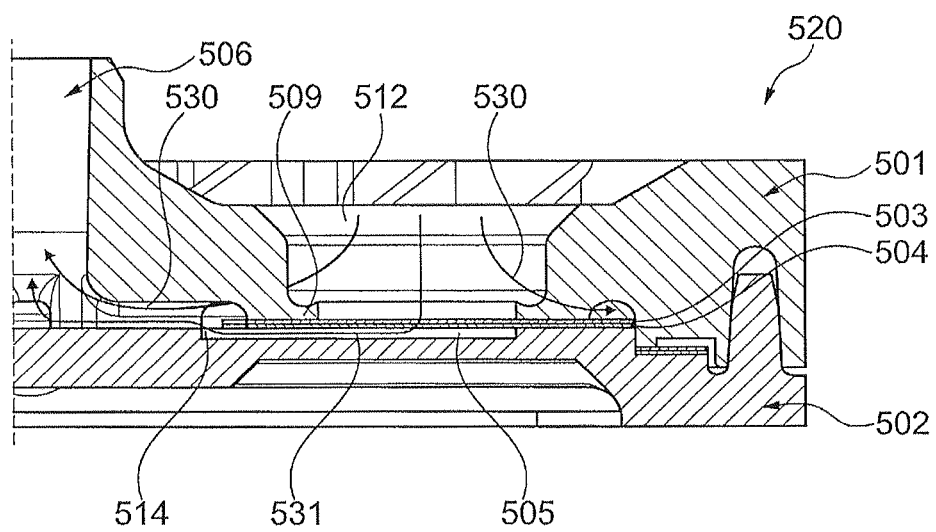
FIG. 9 shows a migration device in accordance with a further exemplary embodiment of the invention.

FIG. 9 shows a migration device 520 in accordance with a further exemplary embodiment of the invention. It is shown that a groove is formed in the lower part 502, which groove forms a first discharge structure. In the upper part there are openings (not shown explicitly) contained in the side wall of the sample chamber 512, which openings form a second discharge structure. The groove 505 and the openings in the side wall are fluid-mechanically connected to the fluid channel, which constitutes the first fluid channel defined within the context of the invention. The groove 505 is connected to the fluid channel by means of the connection point 514. In addition, arrows 530 and 531 are shown, which indicate the flow of the fluid as it is sucked. The arrow 530 shows the flow of the fluid sucked through the openings formed in the side wall, and the arrow 531 shows the flow of the fluid sucked through the groove 505.

Figure 10:
FIG. 10 shows a flow diagram for a method for operating a migration device in accordance with an exemplary embodiment of the invention.

FIG. 10 shows a flow diagram for a method for operating a migration device in accordance with an exemplary embodiment of the invention. The method includes the step S1 of providing a migration device having a sample chamber, a migration matrix, and a discharge structure for discharging a fluid from the migration device to a fluid outlet of the migration device. Furthermore, the method comprises the step S2 of discharging a fluid from the sample chamber and/or from the migration matrix, through the discharge structure, to the fluid outlet.

Figure 11:
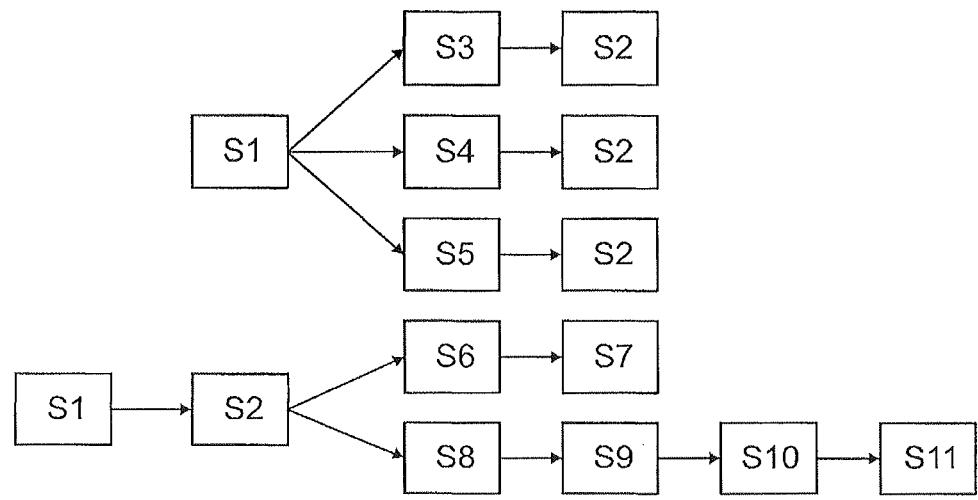
FIG. 11 shows a plurality of flow diagrams for methods according to exemplary embodiments of the invention.

FIG. 11 shows various flow diagrams for various methods according to exemplary embodiments of the invention.

One exemplary embodiment of the invention relates to a method for removing a sample or a treatment liquid, comprising the step S1 of providing the migration device, the step S3 of introducing the sample or the treatment liquid into the sample chamber, and the step S2 of discharging a fluid from the sample chamber and/or from the migration matrix through the discharge structure to the fluid outlet for discharging at least some of the sample or at least some of the treatment liquid through the discharge structure.

A further exemplary embodiment of the invention relates to a method for rinsing the migration device, comprising the step of providing the migration device S1, the step S4 of introducing a rinsing liquid into the sample chamber, and the step S2 of discharging at least some of the rinsing liquid through the discharge structure.

A further exemplary embodiment of the invention relates to a method for drying the migration device, comprising the step S1 of providing the migration device, the step S5 of introducing air through a through-opening of the migration device into the sample chamber by sucking said air through the discharge structure, and the step S2 of discharging the sucked air through the discharge structure.

A further exemplary embodiment of the invention relates to a method for preparing a migration device for an optical examination of the migration matrix, including the steps S1 and S2, which are described above in greater detail. In addition, the method comprises the step S6 of introducing a liquid having a refractive index that corresponds to that of the migration matrix, by the step S7 of introducing a needle through an inlet opening of the migration device into the migration matrix, so that the needle penetrates through the matrix and at least in part into the discharge structure for discharging fluids.

A further exemplary embodiment of the invention relates to a method for migration analysis, comprising the steps S1 and S2 as described above. In addition, the method includes the step S8 of introducing a sample liquid into the sample chamber, the step S9 of fixing cells of the sample liquid by introducing a fixing liquid, the step S10 of staining the cells by introducing a staining liquid into the sample chamber, and the step S11 of optically measuring a migration ability of the cells, wherein all steps of this method are performed using the same migration device.

Figure 12:
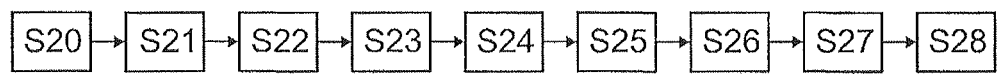
FIG. 12 shows a flow diagram for a method for the migration analysis in accordance with an exemplary embodiment of the invention.

FIG. 12 shows a method for migration analysis in accordance with a further exemplary embodiment of the invention. The method comprises the step S20 of migration preparation, the step S21 of migration, the step S22 of fixing, the step S23 of lysis, the step S24 of staining, the step S25 of clearing the background, the step S26 of neutralisation, the step S27 of drying, and the step S28 of optical measurement, which will be described in greater detail hereinafter.

To provide further detail, in the case of the migration analysis by means of the migration device which is shown for example in FIG. 5A to FIG. 5F, the following approach can be adopted:

The step S20 of migration preparation can comprise the following sub-steps:
a) removing the migration device 520 comprising the upper part 501, lower part 502, and the matrices 503, 504 from a sterile packaging;
b) pre-heating or controlling the temperature of the migration device 520, preferably to 37° C. in a heat cabinet or incubator.

The step S21 of migration can comprise the following sub-steps:
a) delivering a defined partial amount of the diluted sample 521 to the sample chambers 512; the matrices 503, 504 can optionally also be pre-wetted with a defined partial amount of the buffer solution prior to the diluted sample being applied;

b) covering the sample chambers 512 for the purpose of minimising the evaporation volume or saturation of the relative humidity in the sample chamber volumes;

c) returning the migration device 520 filled with diluted sample 520 to the heat cabinet or incubator for up to a maximum of 60 minutes, preferably 30 minutes.

The step S22 of fixing can comprise the following sub-steps:

a) after the incubation (S21, sub-step c)), fixing the migration cells for example with formaldehyde by filling the remaining volume of the sample chamber 512;

This process optionally can also be accelerated in time by emptying the sample chamber 512 after a short reaction time and re-filling it with formaldehyde;

b) emptying the sample chamber 512 into the central suction nipple 506, preferably by means of the clamping ring orifices 517, the annular channel 519, and the fluid channel 518.

The step S23 of lysis can comprise the following sub-steps:

a) lysing the remaining residual red blood bodies, not sucked or not already lysed, on the surface of the migration matrix 503 by filling the sample chambers 512 for example with deionised water or alternative reagents and allowing a reaction time lasting several minutes to pass.

b) emptying c) droplet washing: rinsing the matrices 503, 504 filled with reagent and rinsing the fluid film, which is caused due to the design, on the surface of the migration matrix 503 with deionised water and/or performing intermediate washing processes, metered drop by drop, by alternate suction of air and water by means of the clamping ring orifices 517 and simultaneously by means of the groove 505;

d) intermediate drying: drying the discharge structures 517, 519, 518 or the groove 505 and the matrices 503, 504 over a short period of time by suction of air, which preferably is heated.

The step S24 of staining can comprise the following sub-steps:

a) filling the sample chambers 512 for example with haematoxylin and allowing a reaction time lasting for several minutes to pass;

sub-step a) optionally can also be performed twice;

b) emptying c) droplet washing (similarly to S23, sub-step c));

d) intermediate drying (similarly to S23, sub-step d)).

The step S25 of clearing the background can comprise the following sub-steps:

a) filling the sample chambers 512 for example with diluted HCl solution and allowing a reaction time lasting for several minutes to pass;

b) emptying;

c) droplet washing (similarly to S23, sub-step c));

The step S26 of neutralisation (blueing) can contain the following sub-steps:

a) filling the sample chambers 512 with neutralisation buffer (pH 9) and allowing a reaction time lasting for several minutes to pass;

b) emptying;

c) droplet washing (similarly to S23, sub-step c));

d) optionally: each of these processes (lysis, staining, clearing, neutralisation with subsequent emptying, droplet washing and intermediate drying) can also be performed a number of times in succession, depending on the success of the process.

The step S27 of drying can contain the following sub-steps:

a) drying the discharge structures 517, 519, 518 and the groove 505 and the matrices 503, 504 over a prolonged period of time by suction of air, which preferably is heated;

b) removing the dried migration device 520 from the heat cabinet or incubator;

c) storing the dried migration device 520 until the measurement (maximum 1 year).

The step S28 of optical measurement can contain the following sub-steps:

Producing the transparency:

a) preparing the matrices 503, 504 for the optical measurement by introducing immersion oil 515 using a needle 507 that tapers, for example an injection needle, in that the tapering part of the needle tip penetrates both matrices in the region of the groove 505 of the sub-base and at the same time can infiltrate the reagent laterally in and beneath both matrices (see FIG. 5F). This process can be improved further still by turning the needle as it is introduced and/or by applying negative pressure at the same time at the groove 505;

Measurement:

b) placing the migration device in a 3D transmitted light/reflected light microscope;

c) optically measuring the migration matrix 503 arranged in the migration device.

It should also be mentioned that the terms "comprising" and "having" do not exclude any other elements, and the terms "one" and "a" do not rule out a plurality. It should also be noted that features that have been described with reference to one of the above exemplary embodiments or variants can also be used in combination with other features of other above-described exemplary embodiments or variants. Reference signs in the claims relating to the device or the method are not considered to be limiting either.

The invention claimed is:

1. A migration device for determining the migration ability of ameboidally mobile cells, the migration device comprising:

a sample chamber disposed in a housing, the sample chamber including an inlet port configured and arranged for receiving a sample fluid containing the ameboidally mobile cells;

at least one thin layer migration matrix laying on a bottom surface of the sample chamber and into which the ameboidally mobile cells penetrate, wherein the average pore size of the at least one migration matrix is smaller than the average diameter of the ameboidally mobile cells;

a first discharge structure formed in the housing, the first discharge structure configured and arranged to discharge a fluid from the at least one migration matrix, the first discharge structure having a drain structure disposed in the bottom surface of the sample chamber, second discharge structure formed in the housing, the second discharge structure configured and arranged to discharge a fluid from the sample chamber, the second discharge structure including at least one opening in a side wall of the sample chamber, an annular fluid channel, wherein the annular fluid channel is arranged around the sample chamber, and a fluid connection between the at least one opening in the side wall and the annular fluid channel; and at least one fluid outlet into which the first and the second discharge structure opens.

2. The migration device according to claim 1, wherein the first and second discharge structures are configured and arranged to discharge a fluid out of the housing.

3. The migration device according to claim 1, wherein the at least one migration matrix rests on the bottom surface with a deposit matrix interposed.

4. The migration device according to claim 1, wherein the first discharge structure formed in the bottom surface has a groove arranged in the bottom surface or a groove system and which occupies a proportion of less than 20% of the bottom surface.

5. The migration device according to claim 4, wherein the groove system occupies a proportion of less than 10% of the bottom surface.

6. The migration device according to claim 1, wherein the first discharge structure comprises a first fluid channel arranged in the migration device which passes through from the sample chamber to the fluid outlet.

7. The migration device according to claim 2, wherein the sample chamber is delimited by a side wall, and wherein the second discharge structure comprises:

at least one opening arranged in the side wall of the sample chamber for suction of fluids from the sample chamber, and a fluid connection between the annular fluid channel and the fluid outlet.

8. The migration device according to claim 7, wherein parts of the first discharge structure formed in the bottom surface and the at least one opening arranged in the side wall are connected to the same fluid outlet, and wherein the parts of the discharge structure formed in the bottom surface and the at least one opening arranged in the side wall are connected in series or parallel with regard to their fluid connection.

9. The migration device according to claim 7, wherein the migration device has at least two separate fluid outlets, and wherein parts of the first discharge structure formed in the bottom surface and the opening arranged in the side wall are connected to the two separate fluid outlets.

10. The migration device according to claim 1, comprising:

an upper part, comprising:
a through-opening spatially delimited from a side wall;
a first receiving area;

a lower part, comprising a second receiving area;

wherein the upper part and the lower part are joined together in an assembled state of the migration device;

wherein in the assembled state of the migration device, the at least one migration matrix is arranged between the first receiving area and in the second receiving area;

wherein the through-opening together with the side wall forms the sample chamber and the lower part forms a bottom of the sample chamber, wherein the at least one migration matrix is arranged on the bottom; and wherein the lower part comprises parts of the discharge structure.

11. The migration device according to claim 10, wherein the first discharge structure comprises a groove arranged in the lower part, wherein the groove is arranged at least in part in the second receiving area, so that the groove in the assembled state of the migration device is covered by the migration matrix.

12. The migration device according to claim 10, wherein the deposit matrix is interposed with the at least one migration matrix.

* * * * *